United States Patent
Williams et al.

(10) Patent No.: US 7,179,632 B2
(45) Date of Patent: Feb. 20, 2007

(54) PROCESS FOR THE PRODUCTION OF ALLICIN

(75) Inventors: David Michael Williams, Cardiff (GB); Chandra Mohan Pant, Cardiff (GB)

(73) Assignee: Neem Biotech Ltd., Cardiff (GB)

( * ) Notice: Subject to any disclaimer, the term of this patent is extended or adjusted under 35 U.S.C. 154(b) by 0 days.

(21) Appl. No.: 10/483,016

(22) PCT Filed: Jul. 4, 2002

(86) PCT No.: PCT/GB02/03083

§ 371 (c)(1),
(2), (4) Date: Jun. 21, 2004

(87) PCT Pub. No.: WO03/004668

PCT Pub. Date: Jan. 16, 2003

(65) Prior Publication Data

US 2004/0247711 A1 Dec. 9, 2004

(30) Foreign Application Priority Data

Jul. 4, 2001 (GB) .................. 0116361.7

(51) Int. Cl.
*C12N 9/88* (2006.01)
*A61K 36/8962* (2006.01)
*C07C 323/22* (2006.01)
*C07C 7/10* (2006.01)
*C07C 2/76* (2006.01)

(52) U.S. Cl. .................. 435/232; 424/754; 568/22; 585/601; 585/833

(58) Field of Classification Search ............. 435/232; 424/754; 568/22; 585/601, 833
See application file for complete search history.

(56) References Cited

U.S. PATENT DOCUMENTS 5,741,932 A * 4/1998 Dressnandt et al. .......... 568/21
5,788,758 A * 8/1998 Sawada et al. ............. 106/493

FOREIGN PATENT DOCUMENTS

WO WO97/39115 10/1997
WO WO 9739115 A1 * 10/1997

OTHER PUBLICATIONS

"Garlic: The Science and Therapeutic Application of *Allium sativum* L. and Related Species", Second Edition, H. P. Koch and L. D. Lawson, eds., Lippincott Williams & Wilkins, Philadephia, 1996, pp. 56-57.*
Kubec et al., "Sulfur-containing volatiles arising by thermal degradation of alliin and deoxyalliin," J Agric Food Chem 45(9):3580-3585, 1997.*
The Merck Index, 10th Ed., M. Windholz et al., eds., Merck & Co., Inc., Rahway, NJ, 1983, p. 40.*

* cited by examiner

*Primary Examiner*—Jon Weber
*Assistant Examiner*—Rosanne Kosson
(74) *Attorney, Agent, or Firm*—Williams, Morgan & Amerson, P.C.

(57) ABSTRACT

There is disclosed a method for preparing allicin which comprises the following steps: (a) mechanically treating a natural source of alliinase to release alliinase therefrom; (b) contacting the mechanically treated alliinase source with an aqueous solution of allicin containing alliin at a concentration greater than that found in raw garlic, whereby the alliin is enzymatically converted to allicin by the alliinase released from the alliinase source; and optionally (c) extracting the resultant allicin into a low boiling point non-polar organic solvent.

19 Claims, 4 Drawing Sheets

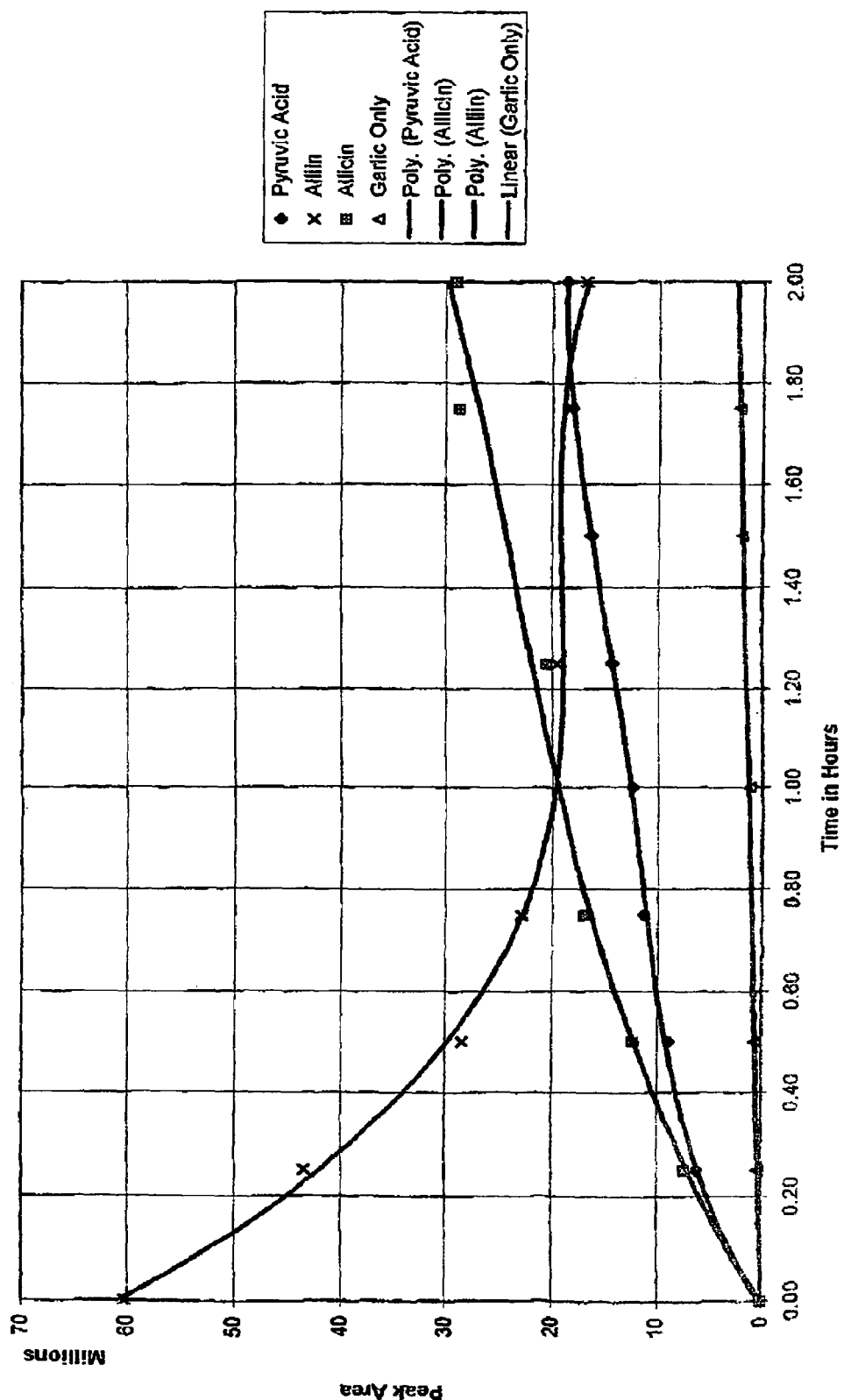

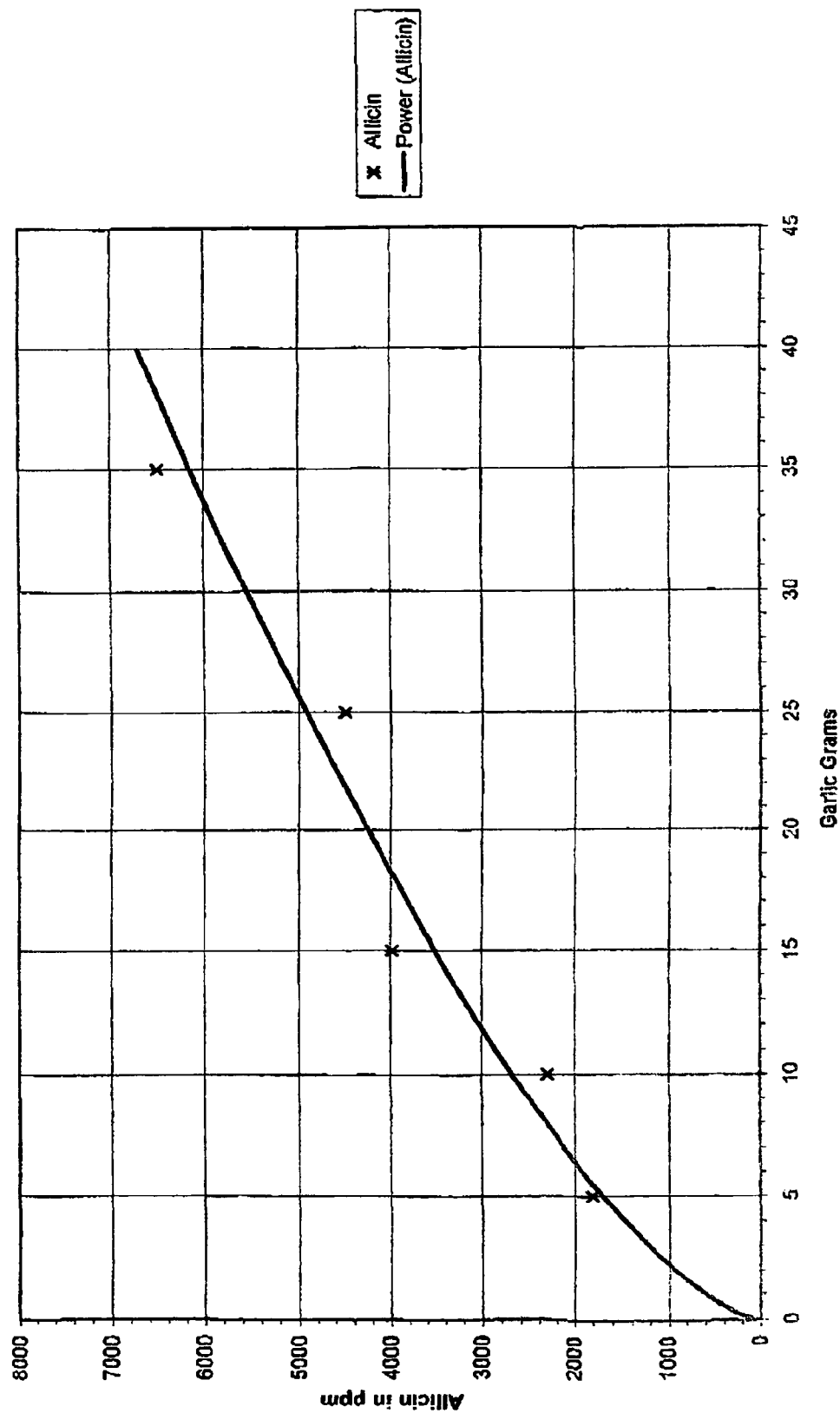
Fig 2 Formation of allicin

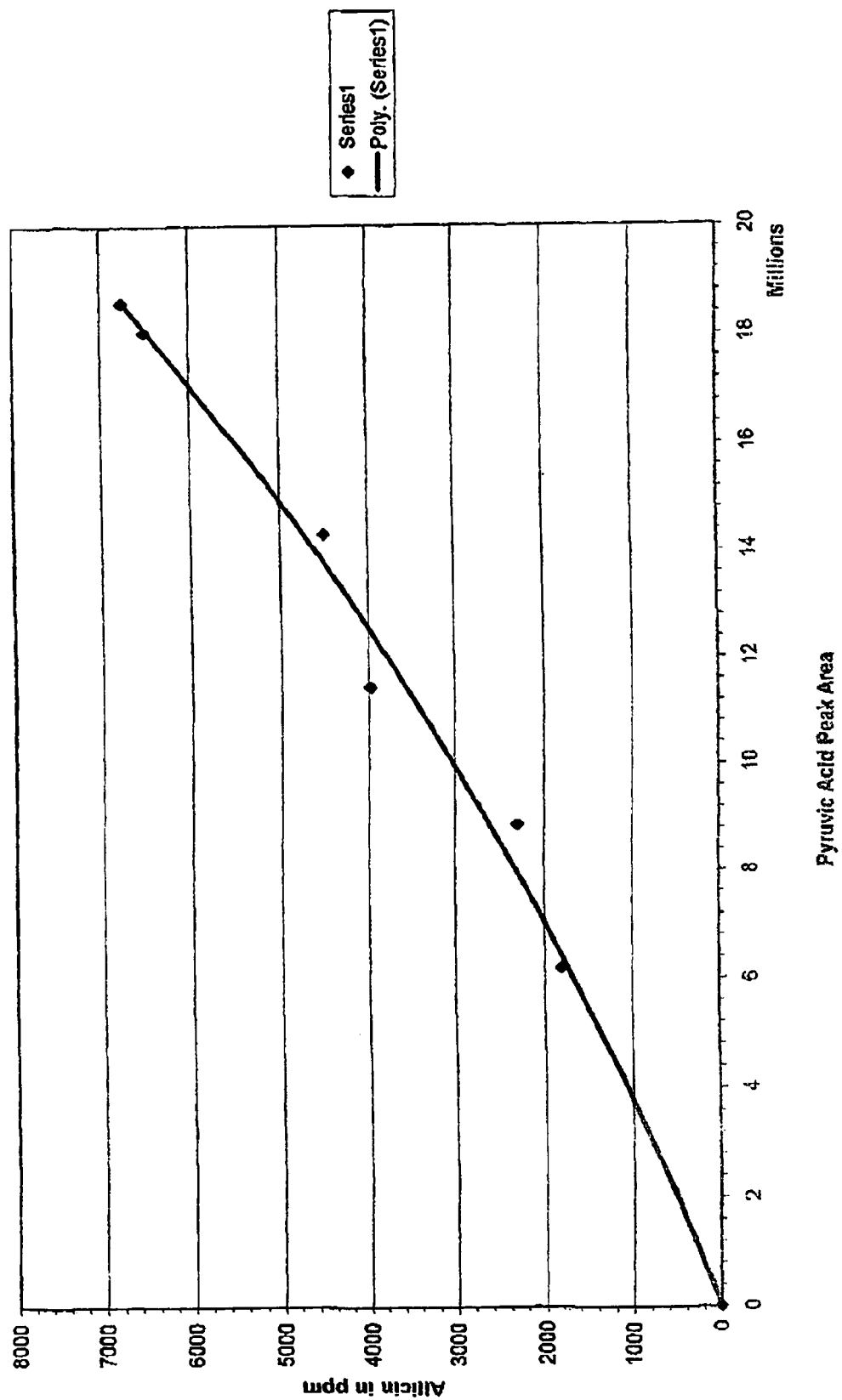

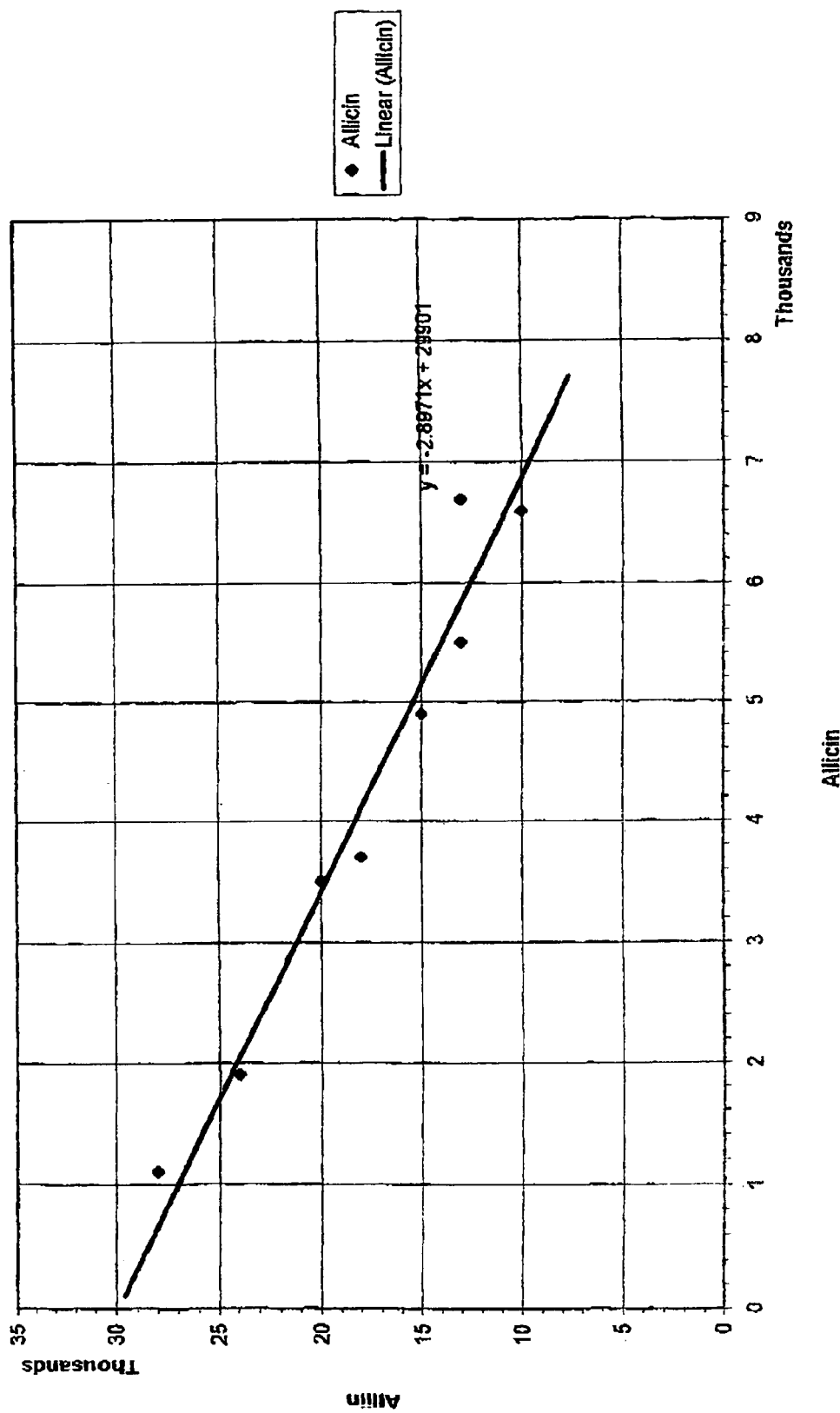
Fig 4 Alliin to Allicin Reaction

PROCESS FOR THE PRODUCTION OF ALLICIN

This application is the U.S. national phase of International Application No. PCT/GB02/03083, filed on Jul. 4, 2002, which claims priority to United Kingdom Application No. GB 0116361.7, filed on Jul. 4, 2001.

The present invention relates to a process for the production of allicin from alliin, and a method for the preparation of pure allicin.

Garlic and onions are members of the lily family. Many medical properties have been ascribed to garlic and onions and they have been used in folk medicine for thousands of years.

A large spectrum of medical properties has been ascribed to garlic, *Allium Sativum*, (Block E 1985) Sci. Am. 252 (3): 114–119). In modern times the interest in the therapeutic properties of garlic has been revived, and it is the object of an increasing number of biochemical and clinical studies. An extensive review of the beneficial properties of garlic extracts may be found in WO99/21008.

Garlic preparations are commercially available in the form of garlic oil, extracts, pills or tablets. Usually the preparation procedures of such garlic preparations are unknown, and the composition and amount of their active ingredients are not defined.

The active principles present in garlic have been found to be sulphur-containing compounds. The principal component of a colourless oil obtained from steam distillates of garlic extracts was shown to be allicin, an unusual sulphur compound of formula $C_6H_{10}S_2O$ (thio-2-propene-1-sulfinic acid S-allyl ester) (Cavallito et al., (1944) J. Am. Chem. Soc. 66, 1944–1954). Allicin was found to be a chemically unstable, colourless to straw coloured liquid. This liquid is thought to be responsible for both the odour and much of the biological activity of garlic.

Although allicin is responsible for the smell of garlic, a garlic bulb exhibits little or no odour until it is cut or crushed. The intact garlic clove does not contain allicin but rather its odourless precursor alliin (+)(S-allyl-L-cysteine sulfoxide). This is converted to allicin, pyruvate and ammonia by a C-S-lyase present in the garlic plant termed alliin lyase or alliinase (Stoll and Seebeck, 1949 Helv Chim Acta 32: 197–205). Alliin and alliinase are found in different compartments of the garlic clove and the cutting or crushing of the clove releases the enzyme allowing it to come into contact with the precursor of allicin.

Allicin is unstable and breaks down into a number of different compounds some of which are thought to be of pharmaceutical use. A list of the various compounds present in garlic and their reported activity is given in Dr. Duke's Phytochemical and Ethnobotanical Database for *Allium sativum*. The main compounds of interest, in addition to alliin and allicin, are the (E/Z)Ajoenes and the various dithiins.

Despite the impressive effect of garlic, studies have been limited by several factors such as lack of controlled methods and suitable double blind studies, and use of preparations with unknown amounts and chemical identification of the active agent. Allicin has been shown to exhibit the beneficial properties ascribed to garlic and thus it would be useful to be able to produce allicin in controlled and known amounts for use as the active ingredient of pharmaceutical compositions. However, allicin is a very labile and volatile compound when exposed to air and methods known today for its preparation are not satisfactory. The chemical synthesis involves many steps and is complicated, laborious, expensive, and very inefficient.

The use of an enzymatic method for producing allicin has been described as seeming to be "attractive", see WO97/39115. However, the so-called "suicidal" nature of the enzyme, namely that it is rapidly and irreversibly rendered inactive by its own reaction product allicin, led the inventors of WO97/39115 to propose the use of an immobilized form of alliinase which is not inactivated by allicin.

The present invention offers an alternative method for the production of allicin, which is simple and inexpensive. By the use of the process of the invention it is possible economically to synthesis pure pharmaceutical grade allicin. The present invention also provides a method for the volume production of the ajoenes and dithiins as a consequence of being able to volume produce allicin. Previous methods have relied on the production of synthetic allicin.

According to a first aspect of the present invention, there is provided a method for preparing allicin which comprises the following steps:

(a) mechanically treating a natural source of alliinase to release alliinase therefrom;

(b) contacting the mechanically treated alliinase source with an aqueous solution of alliin containing alliin at a concentration greater than that found in raw garlic, whereby the alliin is enzymatically converted to allicin by the alliinase released from the alliinase source; and optionally (c) extracting the resultant allicin into a low boiling point non-polar organic solvent.

DESCRIPTION OF THE DRAWINGS

The following drawings form part of the present specification and are included to demonstrate certain aspects of the present invention. The invention may be better understood by reference to one or more of these drawings in combination with the detailed description of specific embodiments presented herein.

FIG. 1 shows the reduction in the reaction rate of alliinase in solutions containing high levels of allicin.

FIG. 2 shows the formation of allicin for a given amount of alliin with increasing addition of garlic.

FIG. 3 shows the formation of pyruvic acid during the conversion of alliin to allicin.

FIG. 4 shows a series of traces showing the growth of the allicin peak and the concurrent disappearance of the alliin peak.

Alliin exists in raw garlic at a concentration of around 0.4 to 0.9%, and varies significantly depending on the growth conditions of the garlic bulbs, which can vary from year to year.

Preferably, alliin is used in the method of the present invention at a minimum concentration of 1%, more preferably of 5%, more preferably still of 10% and most preferably at a minimum concentration of 15%.

Alliin is freely soluble in water and can therefore be used in the method of the present invention at high concentrations. Preferably, alliin is used at a maximum concentration of 50%, more preferably of 40%, more preferably still of 30% and most preferably at a maximum concentration of 25%.

Preferably, alliin is used in the method of the present invention at a concentration of between 10% and 30%, more preferably at a concentration of between 15% and 25%. More preferably still, alliin is used in the method of the present invention at a concentration of around 20%. Use of alliin at a concentration of around 20% in the method of the present invention results in the production of an allicin solution with a concentration of around 1%.

Both the L form and the R form of alliin are converted to allicin by allinase. However, the L-form is converted at a slightly faster rate than the R-form.

The two forms of alliin require derivatising to be resolved. However, the presence of allicin in the reaction mixture interferes with the reaction using a derivatising agent. The observation that, as the conversion of alliin to allicin progresses, the HPLC alliin peak completely disappears, leads to the conclusion that both isomers of alliin are converted to allicin during the reaction. Further, under some conditions, the alliin peak appears as two partially resolved peaks, the sum of which is equal to traces showing only one peak. FIG. 4 shows a series of traces showing the growth of the allicin peak and the concurrent disappearance of the alliin peak Step c), extraction using a low boiling point non-polar organic solvent is necessary in the preparation of pure allicin. However, in cases where some naturally occurring compounds other than allicin can be tolerated, the solution is diluted to approximately it allicin for storage at below −20° C., where it remains stable for several months. In the extraction step, the addition of a low boiling point non-polar solvent prevents the presence of allicin leading to the denaturation of the allinase enzyme.

The extraction step has the advantage of purifying the allicin away from the crushed plant matter, thereby avoiding the potential presence of bacteria in the allicin solution. The extraction step also has the effect of slightly increasing the yield of allicin from a given amount of alliin and garlic.

The natural source of alliinase used in the process of the present invention may be matter obtained from an *allium* genus plant, typically the bulbous portion thereof. Most preferably it is garlic, *Allium Sativum* which is readily available and cheap and which also has a relatively high concentration of alliinase. However, any variety of garlic which contains sufficient quantities of allinase may be used, for example chinese garlic or elephant garlic. Fresh and/or dried garlic may be used, however, fresh garlic contains higher levels of alliinase. The natural alliinase source may be used in the invention in its raw form, although dry or frozen forms are also acceptable.

The natural plant source of alliinase, typically raw garlic bulbs or cloves which preferably will have been peeled and cleaned, is mechanically treated to release alliinase enzyme which is present within the structure of the natural alliinase source. This mechanical treatment may, for example, be crushing or cutting of the alliinase source. Other suitable methods which release the alliinase are also contemplated. One presently preferred method involves the use of a blender having a rapidly rotating blade which is able to disintegrate the alliinase source within a very short period of time. Any suitable industrial or domestic blender may be used. An advantage of blending is that the garlic cloves are reduced to very small pieces whilst the constituents of the mixture are being thoroughly mixed.

Alternatively, the garlic could be crushed and then added to the all in solution, followed by rapid stirring, However, this is not as efficient as the slow and continuous addition of garlic to the blender and produces a lower yield of allicin. It appears that the highest yields of allicin result from the addition of garlic at regular intervals combined with rapid blending and stirring. The allinase in the garlic reacts very quickly with the alliin before becoming inhibited by the presence of allicin, and the more allicin present, the greater the inhibition, as demonstrated by the reduction in reaction rate with solutions containing high levels of allicin, in FIG. 1.

Preferably, the production of allicin is carried out at a temperature of between about 25 and 45° C. More preferably, the production of allicin is carried out at a temperature of between about 30 and 40° C. and most preferably at a temperature of 35° C.

The regular addition of garlic is preferably carried out over a period of at least one hour and more preferably over a period of between about 1 and 2 hours, and most preferably over a period of around 90 minutes.

The alliin solution may be made by dissolving crystalline alliin in water, preferably pure distilled water. Alternatively, the alliin can be formed in situ by oxidation, for example using hydrogen peroxide, of a solution of deoxyalliin of the appropriate strength (Iberyl et al (1990). *Plant Medica* 56). The concentration of the alliin solution may preferably be up to 20% w/v. A typical concentration which may be used in the invention is about 10% w/v. FIG. 4 is a graph showing how the level of allicin produced from alliin varies depending on the level of alliin present in solution.

In accordance with the invention, the mechanically treated alliinase source is contacted with an aqueous solution of alliin. This may be accomplished either by carrying out the mechanical treatment prior to the contacting step or, more preferably, by carrying out the mechanical treatment of the alliinase source within the alliin solution so that, when the alliinase is released, it is available for immediate reaction with the alliin. In this embodiment, where the natural source of alliinase is raw garlic cloves, the preferred mode of mechanical treatment is rapid blending which is preferably carried out for at least 30 seconds, preferably at least 1 minute and most preferably at least 5 minutes. In preferred aspects of this embodiment, the blending is continued throughout the whole of the contacting step.

In this embodiment, it is possible for the alliinase source such as garlic cloves to be added to the solution in more than one stage. Thus, after carrying out the contacting step for a first period of time, a further portion or portions of the alliinase source may be added to the solution and mechanically treated (e.g. blended with a blender) to release the alliinase therefrom, and the contacting step carried out for a second or further period of time. Preferably, the garlic is added slowly in several stages, for example, every 5 minutes, over a prolonged period of time, for example, over a period of up to 3 hours, more preferably less than 2 hours.

Where the mechanical treatment is carried out prior to the contacting step, it is in most cases necessary to bring the mechanically treated material into contact with the alliin solution within a relatively short period of time, before the released alliinase is significantly inactivated by allicin which is concurrently released with the alliinase. Typically, therefore, the material is added to the alliin solution and then immediately mechanically treated to release the allinase and allow the released allinase to immediately contact the alliin. If the material is mechanically treated before contact with the alliin solution, any alliin present in the material may react with the allinase released by the mechanical treatment, to produce allicin which will inhibit the allinase enzyme.

The mechanically treated alliinase source is contacted with the alliin solution for a time and at a temperature such that alliin is converted, by the enzymatic action of the alliinase, to allicin. Thus, for example, the mechanically treated alliinase source may be contacted with the alliin solution for a period of time of from 2 to 4 hours and at a temperature of between about 20° C. and about 40° C., preferably ambient temperature, i.e. about 25° C. A higher concentration of allicin is produced if the allinase source is added gradually over a period of time rather than the whole source of alliinase being added at one time.

The amount of the alliinase source used is preferably that amount which is necessary to convert substantially all of the alliin in the solution to allicin. Where the alliinase source is garlic, it has been found that this can be achieved using an approximately equal weight of raw garlic to alliin in the solution. The alliin is converted to allicin, and the breakdown products of pyruvic acid, ammonia and carbon dioxide, with a conversion ratio for alliin to allicin of approximately 3:1. This is illustrated by the graph shown in FIG. 4. In addition, the graph of FIG. 3 shows the formation of pyruvic acid during the conversion of alliin to allicin.

The allicin formed in step (b) of the process of the invention is extracted into a low boiling point non-polar organic solvent. This extraction step may be carried out simultaneously with at least a part of the contacting step (b) or alternatively may be carried out after completion of the contacting step. Thus, in one embodiment of the invention, the mechanically treated alliinase source (either previously prepared or formed in situ) is contacted with a mixture of the low boiling point non-polar solvent and the alliin solution. The solvent, which owing to its non-polar nature is not miscible with water, will form a separate layer. On blending, this is dispersed into small droplets throughout the alliin water layer. The allicin is soluble in the solvent layer and is immediately removed from the reaction thereby increasing the life of the enzyme to convert more alliin to allicin. The solution is allowed to separate into two layers and the allicin is recovered from the solvent by evaporation under vacuum to yield substantially pure allicin, which is then diluted and stabilized as required In an alternative embodiment, the resultant product of step (b) containing formed allicin is combined with the organic solvent, whereupon extraction of the allicin into the solvent is accomplished. In this alternative embodiment, the resultant solution of step (b) of the process should preferably be contacted with the solvent immediately after completion of the contacting step, given the unstable nature of the allicin product.

Allicin is extremely unstable at concentrations above 0.5% solution in water. However, allicin is reasonably stable at a concentration of 0.5% solution at −40° C. provided the solution has been filtered to remove impurities. The preferred concentration of allicin in solution after conversion from alliin is around 2%. Further, the stability of the allicin is increased in the presence of a slightly acidic solution. After extraction, with a solvent, to give pure allicin, the allicin must be kept at or below −70° C. and breakdown of the allicin product begins immediately. Therefore, it is preferable to dilute the allicin, in order to increase its stability, as quickly as possible, and preferably within 1 to 2 minutes, where possible. In this embodiment, the solvent will initially form a separate layer. The mixture may then be mixed thoroughly, for example by blending, so that the solvent is dispersed into small droplets throughout the alliin water layer. The allicin is soluble in the solvent layer and is immediately removed from the reaction. The solution is allowed to separate into two layers and the allicin is recovered from the solvent by evaporation under vacuum to yield substantially pure allicin, which is then diluted and stabilized as required.

It is possible, using the method of the invention, and if a sufficient quantity of the alliinase source is employed (in one or more stages if necessary), to convert most of the alliin present in the alliin solution to allicin. FIG. 2 is a graph showing the formation of allicin for a given amount of alliin with increasing addition of garlic. Under suitable HPLC conditions both alliin and allicin can be observed simultaneously allowing the conversion to be closely monitored. This enables the end point of the conversion to be accurately determined and so permits an operator of the process to properly time the next stage or stages of the process, bearing in mind the poor stability of allicin in solution. The conversion of alliin to allicin may be aided by providing a slight excess of alliin in the reaction solution.

In the method of the invention, the allicin is produced very rapidly, with the majority of the alliin typically being converted to allicin, in under 30 minutes. The resulting process is thus suited to being carried out as a batch process with a short cycle time, which will produce a solution with a concentration of up to 1.0% v/v allicin. A solution of this strength is unstable. Accordingly, unless the allicin is extracted into a solvent either in situ or immediately after completion of the contacting step, it should preferably be diluted to less than 0.5% w/v, for example about 0.15% w/v. The diluted solution may be further stabilized by adjusting the pH to about pH 4.5, using known method, for example a suitable buffer such as citric acid. Alternatively, the batch process can be adjusted to produce a solution with a concentration of up to 0.5% v/v allicin, which can be readily stored at −20° C.

In step (c) of the method of the invention, allicin produced by the reaction is extracted into a suitable non-polar solvent. The solvent used should have as low a boiling point as possible, preferably of around 45° C. or lower, to allow rapid removal under vacuum at room temperature, be immiscible in water and have as low a water solubility as possible, whilst having the property of being capable of selectively dissolving allicin and no other constituent present in the solution. Examples of suitable solvents are pentane, hexane and ether. In the preparation of material for pharmaceutical use the choice of solvent is influenced by the EC guidelines relating to residual solvents (CPMP/ICH/283/95). These solvents are set out in MCA Euro Direct Publication No. 283/95 (see Appendix A), which lists 64 solvents with concentration limits and permitted daily intake, and these should be borne in mind when selecting a suitable solvent.

Step (c) of the method of the invention is particularly useful where pure allicin is required, for example, for the subsequent production of ajoene for pharmaceutical use.

The production of allicin from pure alliin and fresh garlic yields a material which is identical to that found in nature; any impurity such as pyruvic acid is found in nature as a result of the normal alliin reaction.

The present invention allows for the production of allicin in significant quantities and at strengths not previously attainable from raw garlic or other published or known method. In order to ensure the purity of the allicin product, a high purity starting material (alliin) should be used, either as a crystalline solid or high purity solution. The use of impure starting materials results in the product being coloured and greatly reduces the yield. Thus, it is a preferred aspect of the present invention that the alliin in step (b) is synthesised by a method in which pure deoxyalliin is oxidised using an oxidising agent such as hydrogen peroxide. Deoxyalliin may be synthesised using the method described by Iberl, Miller and Knobloch (1990) (Planta Med 56; 320–326), which method may be modified by the substitution of allyl chloride in place of allyl bromide. Special care should be given to control of the temperature throughout the reaction if the temperature, is too low, the reaction takes too long to complete and if the temperature is too high, the alliinase enzyme activity is destroyed and any allicin produced rapidly breaks down. The present method ensures that the various impurities present as a result of the synthesis of allicin are avoided, in particular allyl chloride, acetic acid, sodium chloride and hydrogen peroxide at the relevant stages of the synthesis. For example, substituting allyl chloride for allyl bromide results in the production of sodium chloride rather than sodium bromide during the conversion process. It is also desirable to avoid the presence of excess hydrogen peroxide, if possible, as hydrogen peroxide has a tendency to explode during the crystallisation of alliin.

The allicin produced by this invention is substantially the same as naturally produced in garlic and may be used as a food additive or condiment, for example to impart garlic flavour to oil, butter, cheese and the like or as a natural food preservative in the meat and milk industry.

The preparation of allicin in a pure and consistent form will enable it to be used for the manufacture of pharmaceutical compositions for human and veterinary use such as, but not being limited to viral, bacterial, fungal and parasitic infections, high levels of cholesterol and blood lipids, high blood pressure and thrombosis. These pharmaceutical compositions can be made by any standard method. The invention has the advantage of flexibility of solution concentration due to the high strength of the allicin solution produced which can then be diluted to any required concentration.

The pharmaceutical composition of the invention can be used in, but not limited to, the treatment of bacterial infections caused by bacteria of the genera *Staphylococcus, Streptococcus, Vibrio* and *Bacillus*, of fungal infections caused for example by *Candida albicans*, anti-amoebic and in the treatment of, for example, heart disease and arteriosclerosis. Recent studies have confirmed published reports on the antibacterial effectiveness of allicin.

In a further aspect of the invention the allicin is produced and extracted from the solvent layer and converted to ajoene using known methods (Iberl, Winkler and Knobloch, supra), which controls the conditions under which the allicin breaks down. The solution containing the allicin affects the breakdown product formed. 2-proponol or ethanol yields at least 60' (E/Z) ajoene. Specific control of the conversion conditions can yield a ratio of up to 90:10 of E ajoene:Z ajoene, or vice versa. Further, the production of 2-vinyl 1–2 diithin can be controlled via specific control of the conversion conditions.

The present invention provides a method for the production of pure allicin and ajoene. These compounds, produced according to the method of the invention, yield compounds of a pharmaceutical grade compositions for the treatment for, but not limited to viral, bacterial, fungal and parasitic infections, high levels of cholesterol and blood lipids, high blood pressure and thrombosis.

In yet another aspect the invention provides substantially pure allicin or ajoene made in accordance with the method of the invention to be used as food additive, condiment or preservative.

Embodiments of the invention will now be described, by way of example only.

The present invention involves the conversion of pure alliin to allicin by the action of the enzyme alliinase present in, for example, fresh garlic. The allicin so produced can then be used as it is, extracted in a suitable solvent such as ether, pentane or hexane, to give pure Allicin or further processed to convert it to ajoene or diathiin.

In the examples, the following materials and methods are used.

Materials

L Cysteine was obtained from Forum Chemicals complete with a Kosher certificate of manufacture. Garlic was purchased from the local stores, as well as in bulk from wholesale markets and large scale importers. The imported garlic was from Spain and France. All other chemicals and solvents were purchased in the normal manner from usual UK Fine Chemical Suppliers.

HPLC

Analysis of the various compounds was carried out using a Hewlett Packard 1100 chromatograph fitted with an isocratic pump and variable wavelength detector. Chromatographic columns were Genisis C18 reverse phase, 250 mm long×4.6 mm id, 5Å particle size, fitted with a suitable guard column and supplied by Jones Chromatography. The mobile phase was 50% Methanol/50% water. The normal detection wavelength was 210 nM.

EXAMPLE 1

Method for the Production of Pure Crystalline Deoxyalliin

The synthesis of Deoxyalliin was based on the method described by Iberl, Miller and Knobloch (1990) (Planta Med 56; 320–326), but modified and substantially improved by the substitution of allyl chloride in place of allyl bromide, with special care being given to control of the temperature throughout the reaction.

2 kg of L-cysteine hydrochloride monohydrate was dissolved in 2 liters of distilled water and stirred at 20–25° C. A solution of sodium hydroxide consisting of 1.6 kg in 2 liters of distilled water was added dropwise to the stirred reaction mixture over a period of 2 to 4 hrs. 1 liter of allyl chloride was then added slowly to the reaction mixture and the temperature was maintained between 25 and 30° C. To ensure completion, the reaction mixture was stirred for a further hour.

The reaction mixture was cooled to 4° C., then glacial acetic acid was added dropwise. During the addition of the acid, white solid started to separate out from the solution and the solution became very thick and difficult to stir. On completion of the addition of the acid the white solid was separated by filtration and dried.

Purification of the dried cake was carried out by dissolving the dried cake in 4 liters of distilled water, whilst maintaining the solution below 45° C. purified deoxyalliin then began to crystallise and the mixture was cooled to −20° C. to complete the crystallisation.

The solid was filtered off and dried. The resulting cake was washed 4 times with 0.5 liter of cold methanol at −20° C. After each washing the solid was dried to remove as much water as possible. The white solid was further washed 4 times with 5 liters of diethyl ether, and then dried, and finally the solid was dried under vacuum. The reaction yielded 1.61 kg of pure material, a recovery of between 90 and 99%.

EXAMPLE 2

Method for the Production of Alliin

The deoxyalliin produced in the manner described above was used as the starting material for the production of alliin. Two different methods of alliin production are employed depending on the required end use of the alliin. The initial stages of the synthesis are identical. The deoxyalliin is dissolved and oxidised by hydrogen peroxide to form alliin. The control of the temperature is critical and the reaction rate and temperature is controlled by the rate of addition of the hydrogen peroxide. The alliin so produced is a racemic mixture of two isomers, as determined by the HPLC method of Iberl, Müller and Knobloch ((1990), supra) using a derivatising agent.

a) Alliin Liquid 6 liters of water was placed in a 10 liter round bottom flask and 1 kg of deoxyalliin was added while stirring. 500 ml of hydrogen peroxide (30% w/v) was added dropwise and the temperature maintained between 22 and 26° C. during the addition. The reaction mixture was further stirred for 3 hours at room temperature to ensure completion of the reaction.

Deoxyalliin has a retention time of 3.4 minutes, L-cysteine 2.6 minutes, and alliin 2.9 minutes. This allowed the reaction to be followed in detail using HPLC to determine the completion point. A minimum quantity of hydrogen peroxide was used in the reaction and the alliin produced can be either used directly for the production of allicin or crystallised to produce pure solid alliin.

b) Solid Crystalline Alliin 1 kg of Deoxyalliin produced according to Example 1, was stirred in 1 liter water and 2 liter Methanol. 0.5 liters of Hydrogen peroxide was added dropwise while maintaining the temperature between 24–26° C. After the addition was complete the reaction mixture was further stirred for 4 hours to ensure completion of the reaction. The solution was refrigerated and cooled to −20° C. to crystallise the Alliin. The white solid was filtered and washed 3 times with 1 liter of cold Methanol (−20° C.). A total of 3 liters of Methanol was used to remove water. The white solid was further washed with 2 liters of Diethyl ether to remove traces of Methanol. The solid material was dried under vacuum to yield a weight of 0.95 kg.

Pure Alliin so produced has been used as a standard for the HPLC monitoring of the various reactions.

EXAMPLE 3

Method for the Production of an Allicin Solution Containing 1% Allicin, Batch Size 0.5 Liter Allicin is produced from the Alliin, prepared by the method detailed in (d), by the simple procedure of either dissolving in distilled water or taking a given amount of the liquid Alliin produced above and adding a small amount of fresh garlic in the form a pealed complete whole clove. The mixture is then combined in a blender for up to 5 minutes, typically 2 minutes, resulting in the complete disintegration of the garlic clove and the release of the garlic enzyme Alliinase. Conversion of the Alliin present by the enzyme alliinase occurs rapidly with approximately 50% of the Alliin being converted. Further additions of garlic result in a further conversion of Alliin to Allicin. The HPLC method described by Iberl, Müller and Knobloch (1990) using a derivatising agent showed that both isomers of Alliin were converted to Allicin and substantially all Alliin present could be converted to Allicin. While the activity of the enzyme rapidly decreased following addition some activity remained for up to 24 hours, as demonstrated by FIG. 1, with the Allicin increasing and the Alliin decreasing with time without further addition of the enzyme. Storage of the reaction mixture at 20° C. did not completely stop the reaction.

The solution so produced can have a strength up to 2% Allicin depending on the starting strength of the Alliin solution, which requires immediate dilution to below 0.5%, typically 0.15% (1500 ppm), to render it stable. Control of the pH to approximately pH 4.5 increases the stability.

a) From Solid Crystalline Alliin:

20 grams of L-Alliin was dissolved in 800 ml of distilled water and 24 grams of Garlic cloves were added slowly over 3 hour period. The reaction mixture was filtered and 200 ml of water was added to briny the solution volume to 1 liter. This was stored at below +4 C.

b) From Deoxyalliin:

An alternative form of this invention is for the allicin produced by the action of the enzyme on alliin to be removed immediately on formation. This is achieved by the addition of a Suitable immiscible organic solvent such as diethyl ether or hexane to the initial mixture before the addition of garlic and blending. On blending the immiscible solvent forms an emulsion with the alliin solution and the allicin as soon as its formed is absorbed by the tiny droplets of solvent so removing it from contact with the enzyme. The aim of this is to preserve and extend the activity of the enzyme so requiring the addition of less garlic. On completion of the conversion of the alliin to allicin the reaction mixture is allowed to separate, the solvent containing the allicin removed and the pure allicin recovered as a straw coloured oily liquid by evaporation of the solvent under vacuum. Immediate dilution is required to prevent the breakdown of the allicin. 5 grams of Alliin yield 1.5 grams of pure allicin, a conversion ratio of 3.3:1.

50 grams of Deoxyalliin, produced according to method listed above was stirred in 225 ml of distilled water and 25 ml of hydrogen peroxide was slowly added. After 4 hrs the deoxyalliin was converted into alliin to yield a 14% (w/v) solution. This alliin solution was converted into 1% Allicin by the addition of whole garlic cloves, filtered and made up to 1.16 liters to yield a 1% solution as above.

EXAMPLE 4

Method for the Production of Pure Allicin Liquid 10 grams of L-Alliin was added to 200 ml of distilled water and 12 grams of fresh garlic cloves were added as described above in (Example 3). When the reaction was complete, after approximately 3 hrs., the reaction mixture was extracted with a suitable solvent such as 50 ml of diethyl ether. The ether layer was separated, dried over Magnesium Sulphate, filtered and evaporated to a straw coloured liquid yielding 1 gram of allicin. This was dissolved in distilled water (100 ml) and the 1% Allicin solution was stored at −20 C.

EXAMPLE 5

Method for the Production of Ajoenes and Dithiins 1 gram of Allicin as prepared above (in Example 4) was dissolved in 10 ml of 40% water-acetone solution and the solution was heated between 63–64 C for 4 hours. The reaction mixture was diluted with 30 ml of 50% water-methanol and washed 5 times with 10 ml of n-pentane. The pentane was kept aside for further processing. The lower water-acetone-methanolic layer was then saturated with ammonium sulphate and extracted with 20 ml dichloromethane. The dichloromethane layer was separated, dried with Magnesium Sulphate, filtered and evaporated to yield crude Ajoene.

The invention claimed is:

1. A method for preparing allicin which comprises the following steps:
   (a) mechanically treating a natural source of alliinase to release alliinase therefrom;
   (b) contacting the mechanically treated alliinase source with an aqueous solution of alliin containing alliin at a concentration greater than that found in raw garlic, whereby the alliin is enzymatically converted to allicin by the alliinase released from the alliinase source; and optionally
   (c) extracting the resultant allicin into a low boiling point non-polar organic solvent wherein the concentration of allicin in solution after the completion of step (b) is from 1% to about 2% w/v.

2. The method of claim 1, wherein the concentration of allicin in solution after the completion of step (b) is about 2% w/v.

3. The method according to claim 1, wherein after completion of step (c), or step (b) if step (c) is not carried out, the allicin is diluted to a concentration of less than 0.5% w/v.

4. The method according to claim 1, wherein after completion of step (c), or step (b) if step (c) is not carried out, the allicin is diluted to a concentration of less than 0.15% w/v.

5. The method according to claim 1, wherein the concentration of alliin is greater than 1% w/v.

6. The method according to claim 1, wherein the alliinase source is an *Allium* genus plant.

7. The method according to claim 6, wherein the *Allium* genus plant is *Allium sativum*.

8. The method according to claim 1, wherein the mechanical treating in step (a) comprises crushing, cutting, or blending.

9. The method according to claim 1, wherein in step (b), contacting the alliinase source with the aqueous source of alliin is carried out in several stages at regular intervals.

10. The method according to claim 9, wherein in step (b), contacting the alliinase source with the aqueous source of alliin comprises blending and stirring for up to 5 minutes.

11. The method according to claim 1, wherein at least step (b) is carried out at a temperature of between 25° C. and 45° C.

12. The method according to claim 11, wherein at least step (b) is carried out at a temperature of between 30° C. and 40° C.

13. The method according to claim 12, wherein at least step (b) is carried out at a temperature of 35° C.

14. The method according to claim 1, wherein at least step (b) is carried out over a period of least 1 hour.

15. The method according to claim 1, wherein step (b) is carried out over a period of between 1 and 2 hours.

16. The method according to claim 1, wherein step (b) is carried out over a 90 minute period.

17. The method according to claim 1, wherein the aqueous source of alliin is provided by dissolving crystalline alliin is distilled water.

18. The method according to claim 1, wherein the aqueous source of alliin is provided by oxidation of a solution of deoxyalliin.

19. The method according to claim 1, wherein the solvent used in step (c) is selected from the group consisting of pentane, hexane and ether.

* * * * *

UNITED STATES PATENT AND TRADEMARK OFFICE
CERTIFICATE OF CORRECTION

PATENT NO. : 7,179,632 B2 Page 1 of 1
APPLICATION NO. : 10/483016
DATED : February 20, 2007
INVENTOR(S) : David Michael Williams and Chandra Mohan Pant It is certified that error appears in the above-identified patent and that said Letters Patent is hereby corrected as shown below:

In column 12, claim 14, line 16, insert -- at -- between "of" and "least".

In column 12, claim 17, line 22, delete the second instance of "is" and insert -- in --.

Signed and Sealed this

Twenty-eighth Day of August, 2007

JON W. DUDAS
*Director of the United States Patent and Trademark Office*